ns Patent [19]

Martin

[11] Patent Number: 4,521,593
[45] Date of Patent: Jun. 4, 1985

[54] PROCESS FOR OBTAINING LACTO-N-NORHEXAOSYL CERAMIDE

[75] Inventor: Michel Martin, Geneva, Switzerland

[73] Assignee: Laboratoire Lucchini S.A., Geneva, Switzerland

[21] Appl. No.: 450,183

[22] Filed: Dec. 15, 1982

[30] Foreign Application Priority Data

Dec. 17, 1981 [CH] Switzerland ................ 8056/81

[51] Int. Cl.$^3$ .............................................. C07H 1/06
[52] U.S. Cl. .................................... 536/55.3; 536/53; 536/123; 536/124; 536/127
[58] Field of Search ............... 536/124, 127, 53, 55.3

[56] References Cited

PUBLICATIONS

Marcus et al., "Pro. Nat. Acad. Sci. USA", vol. 73, No. 9, pp. 3263–3267, Sep. 1976.
Lemieux et al., "Can. J. Chem., vol. 60, No. 1, pp. 68–75, Jan. 1982.

Primary Examiner—Johnnie R. Brown
Attorney, Agent, or Firm—Emory L. Groff, Jr.

[57] ABSTRACT

From human placental tissue, gangliosides and lacto-N-norhexaosyl ceramide of formula:

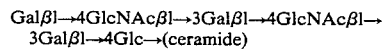

$3Gal\beta1 \rightarrow 4Glc \rightarrow (ceramide)$ are successively extracted.

Lacto-N-norhexaosyl ceramide is used in the diagnosis and treatment of certain tumors and autoimmune diseases.

3 Claims, No Drawings

PROCESS FOR OBTAINING LACTO-N-NORHEXAOSYL CERAMIDE

The use of glycolipids in the diagnosis and treatment of certain autoimmune diseases or certain tumors has suffered from the absence of sufficient and available sources of these compounds until now.

Now, the placenta has proven to be a tissue very rich in Sialyl-lacto-N-norhexaosyl ceramide, whose neutral couple (Gal $\beta$1→4 GlcNAc $\beta$1→3 Gal $\beta$1→4 GlcNAc $\beta$1→3 Gal 1→4 Glc (Ceramide) exhibits a strong i antigenic activity. Thus, the use of lacto-N-norhexaosyl ceramide in the diagnosis and treatment of certain diseases, such as the "cold agglutine disease" or certain tumors, is possible since its preparation in the pure state in sufficient quantity can be obtained from the placenta or placenta residue resulting from the production of $\gamma$-globulins, placental enzymes or extracts. Actually, gangliosides of human placental origin (hematoside-GM3, sialyl-i) contain solely N-acetyl-neuraminic acid in contrast to the gangliosides from tissues of other maamals which contain variable quantities depending on the type of N-glycolyl-neuraminic acid. Further, the residual lipids obtained in this preparation constitute a considerable source of phospholipids of human origin whose use in therapeutics is more and more important as a medium for specific medications, or of lipids that can be used for therapeutic or cosmetic purposes.

The extraction of this antigenic glycolipid can be done either on the residue after the extraction of the $\gamma$-globulins, or on the preparation residue of the placental enzymes or extracts, or on the entire placenta.

EXAMPLE 1

1 kg of placenta or placental residue is ground into 7.5 l of chloroform-methanol (2:1, v/v), everything is left in contact 2 hours at ambient temperature, then filtered. The extract is kept and the solid residue is dissolved in 7.5 of chloroform-methanol mixture (1:1, v/v), reground and left 2 hours at ambient temperature, then filtered. The extract obtained, mixed with the preceding extract, is evaporated in vacuo, thus supplying from 30 to 40 g of dry residue. This residue is redissolved in 2 l of chloroform-methanol (2:1, v/v) to which 400 ml of double distilled water are added, this is stirred and the 2 phases formed are separated by centrifugation or decantation. The aqueous upper phase (extract A) is kept. To the (chloroformic) lower phase are added 650 ml of methanol, which, after stirring, gives a homogeneous solution to which 400 ml of double distilled water are added. After stirring, the two phases are separated as before. The aqueous upper phase is mixed with the first extract A and everything is evaporated after adding toluene or butanol as foam inhibitor. The dry residue obtained of 10 to 20 g contains the major part of the gangliosides of the placenta. The chloroformic phase, after evaporation, supplies from 20 to 30 g of total lipids containing the neutral lipids, the phospholipids and the neutral glycolipids of the placenta.

EXAMPLE 2

1 kg of placenta residue is ground with 2 l of distilled water and 7.2 l of methanol; 3.6 l of chloroform are then added. It is stirred 30 minutes, then filtered. The residue is reextracted, after rehomogenization in 1.3 l of water, by 5.3 l of the chloroform-methanol mixture (1:2, v/v); it is filtered and the 2 extracts are mixed. Then, 3.5 l of double distilled water are added, it is stirred and the 2 phases are separated by centrifugation or decantation. The aqueous upper phase, containing the major part of the gangliosides, is evaporated in vacuo in the presence of butanol as foam inhibitor. The dry residue obtained from the chloroformic phase contains all the other lipids.

EXAMPLE 3

1 kg of ground placenta residue is extracted twice cold by 5 volumes of acetone to remove the neutral lipids. The cleaned tissue is then extracted by reflux with ethanol. The ethanol extract is either concentrated and the glycolipids made to precipitate by cooling to $-4°$ C. for 24 hours, or evaporated dry, then redissolved in the chloroform-methanol mixture (2:1, v/v) and the gangliosides extracted by adding 0.2 volume of water as described in example 1.

To purify it, the dry extract of raw ganglioside is dissolved in 200 ml of 0.2M methanol NaOH and left 2 h at 37° C. After neutralizing, the solution is evaporated dry and the residue dissolved in 100 ml of double distilled water and dialyzed for 48 hours.

The preceding solution is evaporated dry and the residue is redissolved in 20 ml of chloroform-methanol (2:1, v/v), it is filtered to remove the insoluble substance and the gangliosides are precipitated by adding 170 ml of ethyl acetate. The precipitate of about 0.6 to 1 g contains the major part of the gangliosides.

The saponification phase can, however, be abandoned and the dialysis of the raw extract dissolved in water can be performed immediately. The precipitation by ethyl acetate of this extract brings about a stronger proportion of sphingomyelin in the precipitate.

The gangliosides can be purified from this precipitate by dissolving in 100 ml of chloroform-methanol mixture (2:1, v/v) and water extraction as previously described. An aqueous extract of 0.1 to 0.2 g of purified gangliosides is thus obtained consisting mainly of GM$_3$ (hematoside), sialyl-paragloboside and sialyl-lacto-N-norhexaosyl ceramide, in approximately balanced proportions.

It is also possible, from the precipitate of raw gangliosides or from purified gangliosides, to prepare the lacto-N-norhexaosyl ceramide by managed hydrolysis.

The purified gangliosides are dissolved in 20 ml of 0.1N HCl in the methanol-water mixture (80:20, v/v) and left 1 hour at 80° C. Chloroform and water are added to obtain a chloroform-methanol-water mixture 20:10:6 (v/v). The aqueous phase is separated by decantation or centrifugation. A second extraction is performed and the combined aqueous phases are evaporated and supply from 50 to 150 mg of lacto-N-norhexaosyl ceramide containing traces of paragloboside.

This hydrolysis can be obtained by heating at 100° C. for 1 hour gangliosides dissolved in double distilled water to which 1% acetic acid has been added. The purification is also done by division between a chloroform phase and an aqueous phase as previously described.

The purity of the compounds obtained can be verified by chromatography on a plate of H silica gel in the chloroform-methanol-water solvent (60:35:8, v/v) and detection by orcinol-sulfuric acid. The i glycolipid exhibits a characteristic Rf. On the other hand, its i antigenic activity can be measured by inhibition of the hemaglutination by using standard anti-i serums.

The gangliosides also exhibit specific chromatographic behavior. Their identity can be confirmed by hydrolysis with neuraminidase. In the case of sialyl-lacto-N-norhexaosyl ceramide, the appearance of the i antigenic activity can be demonstrated after action of the neuraminidase.

Preferably the gangliosides are chromatographed in a strip on a preparation plate of H silica gel, then a portion of the plate is developed and each of the fractions of gangliosides are eluted in the chloroform-methanol-water mixture (1:2:1.4 v/v). It is evaporated and dissolved with an acetate buffer of pH 5.8 containing 25 U of neuraminidase and 0.1% $CaCl_2$. It is left 24 h at 37° C.; it is evaporated after adding methanol, the residue is dissolved by a mixture of chloroform-methanol-water (60:30:4.5) and the inorganic salts are removed by chromatography on Sephadex G. 25. The chromatography of the eluate on a plate of silica gel as before shows the presence of CDH from the $GM_3$ of paragloboside (PG) from the sialyl-paragloboside (SPG) and the i glycolipid from the hydrolysis of the sialyl-i.

The chloroform phases from the extraction of the gangliosides contain a large proportion of sphingomyelin (SPH) and phosphatidyl-choline (PC) which it is possible to purify.

EXAMPLE 4

50 g of the residue from the chloroform phase after water extraction of the gangliosides, are dissolved in 300 ml of chloroform to which 750 ml of acetone are added and are left overnight at 4° C. The precipitate of 24 g is recovered by centrifugation. After removal of the residual acetone, the precipitate of phospholipids is redissolved in 200 ml of chloroform. This solution is chromatographed on 500 g of basic alumina. The neutral lipids are eluted by 3 l of chloroform, then the sphingomyelin + phosphatidyl-choline mixture is eluted by 4 l of the chloroform-methanol mixture (1:1, v/v). By evaporation, 9.5 to 11 g of a mixture of purified SPH and PC are thus obtained. The mixture is dissolved in 2 l of chloroform-ethyl acetate (1:5, v/v), then subjected to crystallization at −15°. By filtration or centrifugation, 5 to 6 g of precipitate and 3 to 5 g of soluble substance are recovered. The precipitate is redissolved in 2 l of the chloroform-methanol mixture and recrystallized at −15°. Thus, 4 to 5 g of precipitate consisting mainly of SPH are recovered. The soluble fraction thus obtained is mixed with the first and supplies a residue containing, after evaporation, a large proportion of (PC). By recrystallizing the 5 to 6 g of this soluble fraction in 0.8 l of the chloroform-acetone-ethyl acetate mixture (1:5:2, v/v) from 2.5 to 4 g of phosphatidyl-choline, pure in the thin-layer chromatography, is obtained.

The insoluble fraction of sphingomyelin is dissolved in 100 ml of 0.2M methanol NaOH and left from 12 to 24 h at ambient temperature. 100 ml of chloroform are added, it is stirred, then 60 ml of distilled water are added. The chloroform phase is separated to which 50 ml of methanol and 30 ml of double distilled water are added. The chloroform phase is separated by centrifugation or decantation and it is evaporated dry after added ethanol. Thus, 4 to 5 g of SPH are obtained that contain traces of LPC that are removed by recrystallization of this phosphatide in 2 l of chloroform-ethyl acetate (1:5). The 3.5 to 4.5 g of precipitate formed at −15° consist of chromatographically pure SHP.

I claim:

1. A process for obtaining lacto-N-norhexaosyl ceramide of formula:

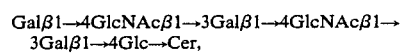

from raw gangliosides isolated from human placental tissue dissolved in an organic solvent wherein the gangliosides are precipitated therefrom by adding ethyl acetate, the impurities remaining in the organic solvent and separating the purified gangliosides, containing in approximately equal proportions sialyl esters of hematoside, paragloboside and lacto-N-norhexaosyl ceramide.

2. A process according to claim 1, wherein the separated mixture of sialyl esters is purified by hydrolysis of said sialyl esters of hematoside, paragloboside and lacto-N-norhexaosyl ceramide and separating from the hydrolysis mixture substantially pure lacto-N-norhexaosyl ceramide.

3. A process according to claim 1, wherein the ethyl acetate is added in a ratio of approximately 8.5 times the volume of the organic solvent.

* * * * *